United States Patent [19]

Dubois et al.

[11] 4,147,655
[45] Apr. 3, 1979

[54] LIQUID CRYSTALS WITH IMPROVED PROPERTIES AND DEVICES USING SUCH LIQUID CRYSTALS

[75] Inventors: Jean-Claude Dubois; Huu T. Nguyen; Annie Zann, all of Paris, France

[73] Assignee: Thomson-CSF, Paris, France

[21] Appl. No.: 868,092

[22] Filed: Jan. 9, 1978

[30] Foreign Application Priority Data

Jan. 14, 1977 [FR] France ................ 77 01068

[51] Int. Cl.² .................. C09K 3/34; G02F 1/13; C07C 69/78; C07C 69/76; C07C 69/62
[52] U.S. Cl. .................. 252/299; 252/408; 260/465 F; 260/465 G; 260/465 H; 260/465 K; 350/350; 560/73; 560/106; 560/107
[58] Field of Search .............. 560/73, 106, 107; 260/465 F, 465 G, 465 H, 465 K; 252/299, 408; 350/350

[56] References Cited

U.S. PATENT DOCUMENTS

| | | | |
|---|---|---|---|
| 3,767,289 | 10/1973 | Aviram et al. | 252/408 |
| 3,876,286 | 4/1975 | Deutscher et al. | 252/299 |
| 3,951,846 | 4/1976 | Cavrilovic | 252/299 |
| 4,002,670 | 1/1977 | Steinstrasser | 252/299 |
| 4,011,008 | 3/1977 | Gerritsma et al. | 252/299 |

FOREIGN PATENT DOCUMENTS 2338542 2/1974 Fed. Rep. of Germany ........... 252/299

OTHER PUBLICATIONS

Nash, J. A., et al., Mol. Cryst. Liq. Cryst., vol. 25, pp. 299–321 (1974).
Gray, G. W., et al., Liquid Crystals & Plastic Crystals, vol. 1, John Wiley & Sons, Inc., pp. 103–150 (1974).

*Primary Examiner*—Benjamin R. Padgett
*Assistant Examiner*—T. S. Gron
*Attorney, Agent, or Firm*—Edwin E. Greigg

[57] ABSTRACT

Novel mesomorphic substances, constituting, in certain temperature ranges, nematic or smectic liquid crystals, are compounds of the formula

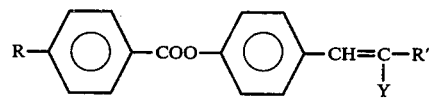

wherein
Y is H or CN;
R is alkyl or alkoxy of 1 to 10 carbon atoms;
R' is alkyl of 1 to 10 carbon atoms or

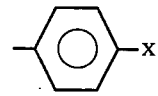

X is Br, Cl or CN.

5 Claims, No Drawings

LIQUID CRYSTALS WITH IMPROVED PROPERTIES AND DEVICES USING SUCH LIQUID CRYSTALS

BACKGROUND OF THE INVENTION

The invention relates to new liquid crystal materials having improved properties, for making display devices. This invention also includes the process of making these liquid crystal products, mixtures of the products thus made with other liquid crystal substances and the devices using the foregoing compounds or mixtures.

Liquid crystals, particularly those having molecular structures of the "twisted nematic" and/or "variable birefringence" type, are useful in display devices.

For use in display devices, liquid crystals having strong positive dielectric anistropy and which are stable over a temperature range as broad as possible including ordinary temperature, are sought.

OBJECT AND SUMMARY OF THE INVENTION

It is an object of the invention to provide liquid crystal materials which have the foregoing properties.

In a compositional aspect, this invention relates to novel compounds of Formula I,

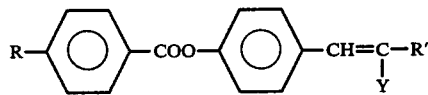

(I)

wherein
Y is H or CN
R is — $C_n H_{2n+1}$ or — $C_n H_{2n+1}$ and
R' is — $C_m H_{2n+1}$ or

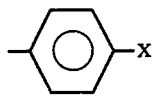

X is Cl, Br or CN and
n and m are integers from 1 to 10.

In another aspect, this invention relates, in a liquid crystal display device containing a liquid crystal composition, to the improvement wherein the liquid crystal composition contains a compound of Formula I.

DETAILED DESCRIPTION

Compounds of this invention correspond to compounds of Formula I(a), wherein Y is H, R is -$OC_nH_{2n+1}$ or -$C_nH_{2n+1}$ and R' is — $C_mH_{2n+1}$, or to compounds of Formula I(b), wherein Y is CN, R is — $OC_nH_{2n+1}$ and R' is

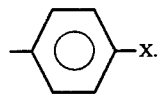

Of compounds of Formula I(a), those are preferred wherein n is 1-8 and R' is of 3-5 carbon atoms.

Of compounds of Formula I(b), those are preferred wherein n is 4-8.

Many of the substances of the Formulas I(a) and I(b) exhibit mesomorphic properties over a very wide temperature range and have melting points close to ordinary temperature. Eutectic mixtures of three or four components have the temperature ranges required for display devices, particularly between 0° C. and +70° C.

The final step of the synthesis of compounds of Formula I is esterification in pyridine medium of an acid chloride and a vinyl phenol, namely:

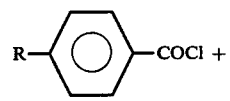

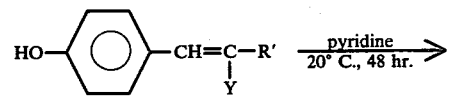

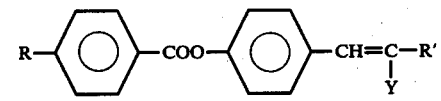

In preparation of the vinyl phenol which is finally converted to a compound of Formula I(a), the first two steps are:

(a) Friedel-Crafts reaction between phenol and a linear aliphatic acid chloride containing R:

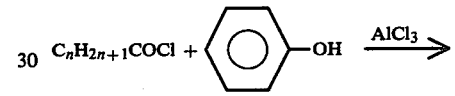

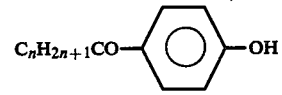

(b) Meerwein-Pondorff-Verley reduction followed by dehydration:

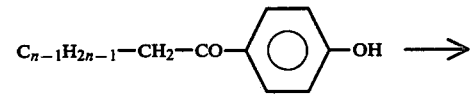

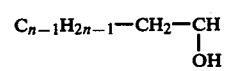

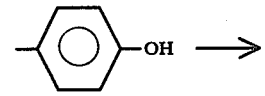

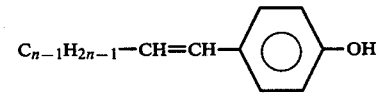

In preparation of the phenol which yields a compound of Formula I(b), the phenol is synthesized in a single step by condensation, in ethanol, of p-hydroxybenzaldehyde with a para-substituted α-cyanotoluene:

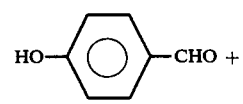

-continued

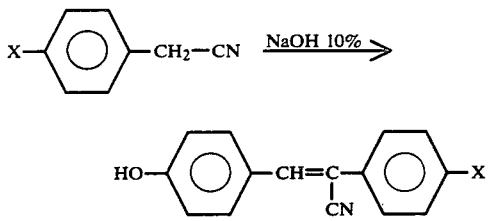

This condensation reaction is known as KNOEVENAGEL reaction, described for instance as the condensation of an aldehyde with an active methylene compound in the presence of a base, catalysed by amines in alcoholic solution.

Compounds of Formula I(a) or I(b) can be used as the sole liquid crystal compound in a liquid display device, but preferably the liquid crystal compositions contain a mixture of at least two compounds of Formula I. Generally, the mixtures contain 2–4 compounds of Formula I, so as to provide eutectic mixtures having nematic properties over a broad temperature range.

A preferred characteristic of mixtures of compounds of Formula I is that the mixtures have properties for use in twisted cell and are therefore highly desirable for use in liquid crystal display devices.

It will be understood that among the preferred liquid crystal devices in accordance with this invention are those adapted for electrooptical display.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by molar fraction.

EXAMPLE 1

There is given below an example of synthesis of a compound of Formula I(a):
4'-(1''-heptenyl)phenyl 4-heptylbenzoate

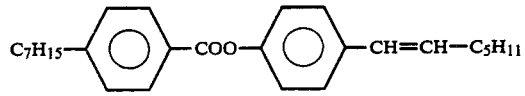

Step (a): synthesis of

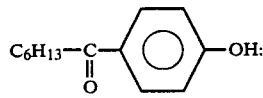

4-heptanoylphenol.

There are charged to a half-liter reactor 9.4 g. (0.1 mole) of phenol in 150 ml. of nitrobenzene. The contents of the reactor are stirred and the mixture is cooled below 5° C. Then 27 g. (0.2 mole) of $AlCl_3$ is added in small portions over ½ hour. The resulting mixture is stirred vigorously and then there is added a solution of 15.5 g. of $C_6H_{13}COCl$ (∼ 0.011 mole) in 50 ml. of nitrobenzene over an hour while the temperature is kept below 5° C. The mixture is stirred at ambient temperature for 12 hours and then the mixture is poured in 100 g. of ice and 50 ml. of concentrated HCl and stirred for ½ hour. The organic fraction is removed by decantation and the aqueous fraction is washed twice with $CCl_4$ (100 ml.). The organic fractions are collected and washed three times with water (to neutrality). The solvent is evaporated under reduced pressure. The organic solution is dried over anhydrous $Na_2SO_4$. The solid obtained is recrystallized in benzene. There are obtained 16.9 g. of pure product (yield 82%), melting point: 93° C.

Step (b): Synthesis of

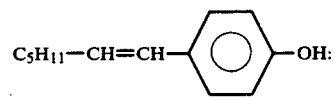

4-(1'-heptenyl)phenol.

There are dissolved 15.5 g. (0.075 mole) of $C_6H_{13}$ —

in 70 ml. of xylene then solution of 14 g. (0.07 mole) of aluminum isopropylate in 80 ml. of isopropyl alcohol is added thereto. The acetone formed during the reaction is removed by distillation at the rate of 4 drops per minute for 6 hours. Then the reaction mixture is poured in a solution containing 25 ml. of concentrated $H_2SO_4$, 100 g. of ice and 50 ml. of water. This mixture is stirred for an hour and extracted with ether. The ether extracts are washed with water to neutrality (pH 6). The organic solution is dried over $Na_2SO_4$ and the solvent is evaporated off. Chromatographic separation on silica with benzene (50%) hexane (50%) mixture is performed. The solid is recrystallized from hexane. There are obtained 8.7 g. of pure product (yield 61%): melting point 67° C.

Final step: synthesis of

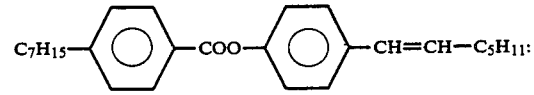

4'-(heptenyl)phenyl 4-heptylbenzoate.

Heptylbenzoyl chloride (530 mg., 0.0022 M), obtained by reaction of heptylbenzoic acid with $SOCl_2$, and 380 mg. of

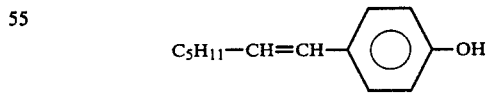

(0.002 M) in 5 ml. of pyridine are allowed to react at ambient temperature for 48 hours. Then the reaction mixture is poured into a solution of 5 ml. of concentrated $H_2SO_4$ and 50 g. of ice. The organic fraction is extracted with ether (3 times, 100 ml. total). The organic fraction is washed with water (3 times) and dried over anhydrous $Na_2SO_4$. The solvent is evaporated and the solid residue is treated by chromatography on silica with a benzene (50%) hexane (50%) mixture. The product is finally recrystallized twice from ethanol. The yield is above 80%.

Properties of pure substances:

By way of examples, tables I, II and III give some properties of pure compounds of the invention. For the sake of simplification, only the values of n and m are indicated for identification of pure substances of Formula I(a) and the value of n and the nature of substituent X for identification of pure materials of Formula I(b).

The numbers indicated in the central part of each table are transition temperatures in degrees centigrade.

TABLE I

Compounds of Formula I(a)

$$C_nH_{2n+1}-\bigcirc-\underset{O}{\overset{\|}{C}}-O-\bigcirc-CH=CH-C_mH_{2m+1}$$

| n | m | K | S | N | I | $\Delta H_f$ (kcal/mol) |
|---|---|---|---|---|---|---|
| 1 | 3 | . 84 | — | — | . 92.5 | . |
| 3 | 3 | . 52.5 | — | — | . 93 | . 4.0 |
| 5 | 3 | . 43 | — | — | . 89 | . 3.75 |
| 6 | 3 | . 43 | — | — | . 80.5 | . |
| 7 | 3 | . 52.5 | — | — | . 83.5 | . 5.65 |
| 8 | 3 | . 51.5 | . | (37) | . 79.5 | . |
| 1 | 5 | . 52.5 | — | — | . 83 | . |
| 3 | 5 | . 47.5 | — | — | . 85 | . 3.9 |
| 5 | 5 | . 43 | — | — | . 85 | . 2.85 |
| 6 | 5 | . 42 | — | — | . 76 | . 3.35 |
| 7 | 5 | . 35 | — | — | . 82.5 | . 6.8 |
| 8 | 5 | . 47.5 | . | (31) | . 77.5 | . |

The temperatures indicated in parentheses correspond to metastable transitions.

The legend of the signs used in this table is as follows:
K: crystalline phase
S: smectic phase
N: nematic phase
I: isotropic liquid phase
· phase exists
− phase does not exist
$\Delta H_f$: melting enthalpy

TABLE II

Compounds of Formula I(a)

$$C_nH_{2n+1}-O-\bigcirc-COO-\bigcirc-CH=CH-C_mH_{2m+1}$$

| n | m | K | S | N | I | $\Delta H_f$ |
|---|---|---|---|---|---|---|
| 1 | 3 | . 88 | — | — | . 130 | . |
| 2 | 3 | . 99 | — | — | . 138 | . |
| 4 | 3 | . 93.5 | — | — | . 127 | . |
| 7 | 3 | . 71.5 | — | — | . 111.5 | . |
| 8 | 3 | . 77 | . | 83 | . 114 | . |
| 1 | 5 | . 53.5 | — | — | . 112.5 | . 6.0 |
| 2 | 5 | . 88 | — | — | . 130 | . |
| 4 | 5 | . 81 | — | — | . 118 | . |
| 7 | 5 | .70.5 | — | — | . 107.5 | . |
| 8 | 5 | . 70 | . | 85 | . 108 | . |

TABLE III

Compounds of Formula I(b)

$$C_nH_{2n+1}O-\bigcirc-COO-\bigcirc-CH=\underset{CN}{C}-\bigcirc-X$$

| n | X | K | N | I |
|---|---|---|---|---|
| 4 | Br | . 162 | . 246 | . |
| 4 | CN | . 149 | . 270 | . |
| 4 | Cl | . 151 | . 241 | . |
| 7 | Br | . 133 | . 220 | . |

TABLE III-continued

Compounds of Formula I(b)

$$C_nH_{2n+1}O-\bigcirc-COO-\bigcirc-CH=\underset{CN}{C}-\bigcirc-X$$

| n | X | K | N | I |
|---|---|---|---|---|
| 7 | CN | . 133.5 | . 242 | . |
| 8 | Br | . 130 | . 214 | . |
| 8 | CN | . 133 | . 237 | . |

The pure compounds of Formula I(a) have a positive dielectric anistropy of about 0.3. The pure compounds of Formula I (b) exhibit a positive dielectric anistropy of about 15, when X is CN.

EXAMPLE 2—PROPERTIES OF MIXTURES (a) An example of an eutectic binary mixture is:

$$C_5H_{11}-\bigcirc-COO-\bigcirc-CH=CH-C_3H_7 : 45 \text{ mole \%}$$

$$C_5H_{11}-\bigcirc-COO-\bigcirc-CH=CH-C_5H_{11}: 55 \text{ mole \%}$$

The mixture is nematic from 6° to 87° C. Such a temperature range is very uncommon for a mixture of two mesomorphic products.

EXAMPLE 3

Using four pure substances of Formula I(a), an eutectic mixture is obtained having a nematic range covering broadly the needs of users, namely, product nematic at least from 0° to 70° C.

|  | (Molar fraction) |
|---|---|
| (a) $C_5H_{11}-\bigcirc-COO-\bigcirc-CH=CH-C_3H_7$ : | (0.32) |
| $C_5H_{11}-\bigcirc-COO-\bigcirc-CH=CH-C_5H_{11}$: | (0.41) |
| $C_7H_{15}-\bigcirc-COO-\bigcirc-CH=CH-C_5H_{11}$: | (0.16) |
| $CH_3O-\bigcirc-COO-\bigcirc-CH=CH-C_5H_{11}$: | (0.11) |

This mixture is nematic from −8.5° C. to +89° C.

|  | (Molar fraction) |
|---|---|
| (b) $C_5H_{11}-\bigcirc-COO-\bigcirc-CH=CH-C_3H_7$ : | (0.25) |
| $C_5H_{11}-\bigcirc-COO-\bigcirc-CH=CH-C_5H_{11}$: | (0.35) |
| $C_6H_{13}-\bigcirc-COO-\bigcirc-CH=CH-C_5H_{11}$: | (0.30) |
| $C_7H_{15}-\bigcirc-COO-\bigcirc-CH=CH-C_5H_{11}$: | (0.10) |

This mixture is nematic from −16.5° C. to +83° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid crystal compound of the formula:

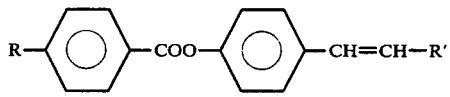

wherein:
R is $-OC_nH_{2n+1}$ or supressing $C_nH_{2n+1}$ and n is an integer from 1 to 10;
R' is alkyl of 1 to 10 carbon atoms.

2. A compound of claim 1, wherein n is from 1 to 8 and R' is of 3 to 5 carbon atoms.

3. A mixture containing at least two compounds of claim 1.

4. The mixture of claim 3, containing the following molar composition:

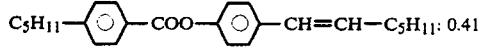

5. The mixture of claim 3, characterized in containing the following molar composition:

* * * * *